(12) United States Patent
Cook (10) Patent No.: US 8,631,796 B2
(45) Date of Patent: *Jan. 21, 2014

(54) LARYNGEAL MASK

(75) Inventor: Daniel J. Cook, Richmond Heights, MO (US)

(73) Assignee: Cookgas, L.L.C., St. Louis, MO (US)

( * ) Notice: Subject to any disclaimer, the term of this patent is extended or adjusted under 35 U.S.C. 154(b) by 2227 days.

This patent is subject to a terminal disclaimer.

(21) Appl. No.: 10/656,653

(22) Filed: Sep. 3, 2003

(65) Prior Publication Data

US 2004/0255953 A1    Dec. 23, 2004

Related U.S. Application Data

(60) Continuation-in-part of application No. 09/829,157, filed on Apr. 9, 2001, now Pat. No. 6,705,321, which is a continuation-in-part of application No. 09/179,928, filed on Oct. 27, 1998, now Pat. No. 6,422,239, which is a division of application No. 08/843,631, filed on Apr. 10, 1997, now Pat. No. 5,937,860.

(51) Int. Cl.
*A61M 16/00* (2006.01)

(52) U.S. Cl.
USPC ................................ 128/207.15; 128/207.14

(58) Field of Classification Search
USPC ........................................ 128/207.15, 207.14
See application file for complete search history.

(56) References Cited

U.S. PATENT DOCUMENTS

| | | | |
|---|---|---|---|
| 678,814 | A | 7/1901 | Riggs |
| 2,335,741 | A | 11/1943 | Contaldi |

(Continued)

FOREIGN PATENT DOCUMENTS

| | | |
|---|---|---|
| EP | 0865789 | 9/1988 |
| EP | 0294200 A3 | 12/1988 |

(Continued)

OTHER PUBLICATIONS

"Products—LMA Fastrach," http://www.Lmana.com/prod/components/products/lma_fastrach.html, printed on Jun. 19, 2005, one page.
"9c Removal of LMA-Fastrach Prior to Extubation," LMA-Fastrach Instructional Manual, www.Lmana.com/docs/fastrach_instruction. pdf, Feb. 2002, pages cover (2 pages), 26-27.
Byrd, Jr., R.P."Ventilation, Mechanical," http://www.emedicine. com/med/topic3370.htm, Jul. 6, 2006, pp. 1-13.

(Continued)

*Primary Examiner* — Darwin Erezo
(74) *Attorney, Agent, or Firm* — Thompson Coburn LLP (57) ABSTRACT

A laryngeal mask of the type used to facilitate lung ventilation and the insertion of endo-tracheal tubes or related medical instruments through a patient's laryngeal opening as used during general anesthesia, intensive care, or critical patient care is described that includes an inflatable positioning and a respiratory tube. The inflatable positioning shield is formed to fit within a patient's oropharynx, and has an inflatable, hollow peripheral portion, a pliable base in fluid communication with the peripheral portion, a shield recess formed after inflation of the peripheral portion, and a rear portion formed between the posterior base and the peripheral portion after inflation of the peripheral portion, wherein the posterior base has a recessed front portion. The respiratory tube has a proximal end lumen, a curved tubular body of sufficient size to permit the passage of endo-tracheal tubes or related medical instruments, and a distal end passing through and secured to the rear portion of the positioning shield. The distal end terminates at a distal lumen, which passes through and is secured to the rear portion of the positioning shield such that tubes and instruments passing through the respiratory tube will be directed into the laryngeal opening.

37 Claims, 8 Drawing Sheets

(56) References Cited

U.S. PATENT DOCUMENTS

| | | |
|---|---|---|
| 2,787,010 A | 4/1957 | Uphoff |
| 3,139,088 A | 6/1964 | Galleher, Jr. |
| 3,434,100 A | 3/1969 | Dykzeul |
| 3,606,669 A | 9/1971 | Kemble |
| 3,734,100 A | 5/1973 | Walk et al. |
| 3,756,601 A | 9/1973 | Frey et al. |
| 3,945,069 A | 3/1976 | Cecil |
| 4,146,034 A | 3/1979 | Gupta |
| 4,231,365 A | 11/1980 | Scarberry |
| 4,327,720 A | 5/1982 | Bronson et al. |
| 4,340,046 A | 7/1982 | Cox |
| 4,388,076 A | 6/1983 | Waters |
| 4,444,201 A | 4/1984 | Itoh |
| 4,509,512 A | 4/1985 | LeClercq |
| 4,509,514 A | 4/1985 | Brain |
| 4,520,810 A | 6/1985 | Weiss |
| RE31,948 E | 7/1985 | Deutsch et al. |
| 4,540,959 A | 9/1985 | Saad |
| 4,582,056 A | 4/1986 | McCorkle, Jr. |
| 4,593,687 A | 6/1986 | Gray |
| 4,661,028 A | 4/1987 | Sanger |
| 4,674,496 A | 6/1987 | Svadjian et al. |
| 4,751,922 A | 6/1988 | DiPietropolo |
| 4,791,923 A | 12/1988 | Shapiro |
| 4,825,861 A | 5/1989 | Koss |
| 4,863,439 A | 9/1989 | Sanderson |
| 4,872,483 A | 10/1989 | Shah |
| 4,895,533 A | 1/1990 | Yagi |
| 4,919,127 A | 4/1990 | Pell |
| 4,995,388 A * | 2/1991 | Brain ............... 128/207.15 |
| 5,024,220 A | 6/1991 | Holmgreen et al. |
| 5,033,919 A | 7/1991 | Choe |
| 5,037,251 A | 8/1991 | Roth |
| 5,042,475 A | 8/1991 | LaBombard |
| 5,071,413 A | 12/1991 | Utterberg |
| 5,197,463 A | 3/1993 | Jeshuran |
| 5,218,970 A | 6/1993 | Turnbull et al. |
| 5,222,487 A | 6/1993 | Carr et al. |
| 5,253,658 A | 10/1993 | King |
| 5,277,178 A | 1/1994 | Dingley |
| 5,279,610 A | 1/1994 | Park et al. |
| 5,282,464 A | 2/1994 | Brain |
| 5,303,697 A | 4/1994 | Brain |
| 5,324,080 A | 6/1994 | McNaughton et al. |
| 5,326,196 A | 7/1994 | Noll |
| 5,340,165 A | 8/1994 | Sheppard |
| 5,355,879 A * | 10/1994 | Brain ............... 128/207.15 |
| 5,391,248 A | 2/1995 | Brain |
| 5,392,774 A | 2/1995 | Sato |
| 5,393,101 A | 2/1995 | Matkovich |
| 5,477,852 A | 12/1995 | Landis et al. |
| 5,509,408 A | 4/1996 | Kurtis |
| 5,513,627 A | 5/1996 | Flam |
| 5,527,316 A | 6/1996 | Stone |
| 5,529,582 A | 6/1996 | Fukuhara |
| 5,545,048 A | 8/1996 | Maeda |
| 5,546,937 A | 8/1996 | Stuart et al. |
| 5,562,371 A | 10/1996 | Reed |
| 5,562,673 A | 10/1996 | Koblish et al. |
| 5,569,222 A | 10/1996 | Haselhorst et al. |
| 5,579,762 A | 12/1996 | Lee |
| 5,584,290 A | 12/1996 | Brain |
| 5,588,424 A | 12/1996 | Insler et al. |
| 5,590,643 A | 1/1997 | Flam |
| 5,623,921 A | 4/1997 | Kigsinger et al. |
| 5,632,271 A | 5/1997 | Brain |
| RE35,531 E * | 6/1997 | Callaghan et al. ....... 128/207.15 |
| 5,643,174 A | 7/1997 | Yamamato et al. |
| 5,653,231 A | 8/1997 | Bell |
| 5,655,519 A | 8/1997 | Alfery |
| 5,682,880 A * | 11/1997 | Brain ............... 128/207.15 |
| 5,711,296 A | 1/1998 | Kolobow |
| 5,713,348 A | 2/1998 | Pell |
| 5,720,749 A | 2/1998 | Rupp |
| 5,743,258 A | 4/1998 | Sato |
| 5,772,643 A | 6/1998 | Howell et al. |
| 5,787,879 A | 8/1998 | Gibson |
| 5,878,745 A | 3/1999 | Brain |
| 5,881,726 A | 3/1999 | Neame |
| 5,896,858 A | 4/1999 | Brain |
| 5,937,860 A | 8/1999 | Cook |
| 5,947,120 A | 9/1999 | Bailey |
| 5,961,489 A | 10/1999 | Hirota |
| 5,979,445 A | 11/1999 | Neam et al. |
| 6,021,779 A | 2/2000 | Pagan |
| 6,196,224 B1 | 3/2001 | Alfery |
| 6,240,922 B1 * | 6/2001 | Pagan ............... 128/207.15 |
| 6,261,401 B1 | 7/2001 | Pagan |
| 6,374,827 B1 | 4/2002 | Bowden et al. |
| 6,386,199 B1 | 5/2002 | Alfery |
| 6,422,239 B1 | 7/2002 | Cook |
| 6,450,164 B1 | 9/2002 | Banner et al. |
| 6,612,305 B2 | 9/2003 | Fauza |
| 6,631,720 B1 | 10/2003 | Brain |
| 6,668,821 B2 | 12/2003 | Christopher |
| 6,705,318 B1 | 3/2004 | Brain |
| 6,705,320 B1 | 3/2004 | Anderson |
| 6,705,321 B2 * | 3/2004 | Cook ............... 128/207.15 |
| 6,705,322 B2 | 3/2004 | Chang |
| 6,729,325 B2 | 5/2004 | Alfery |
| 6,892,731 B2 | 5/2005 | Cook |
| 6,899,147 B2 | 5/2005 | Ogawa et al. |
| 6,923,176 B2 | 8/2005 | Ranzinger |
| 6,935,153 B2 | 8/2005 | Frigo et al. |
| 6,983,744 B2 | 1/2006 | Alfery |
| 7,013,899 B2 | 3/2006 | Alfery |
| 7,021,686 B2 | 4/2006 | Glasgow et al. |
| 7,040,312 B2 | 5/2006 | Alfery et al. |
| 7,040,322 B2 | 5/2006 | Fortuna |
| 7,096,868 B2 | 8/2006 | Tateo et al. |
| 7,097,802 B2 | 8/2006 | Brain |
| 7,128,071 B2 | 10/2006 | Brain |
| 1,345,425 A1 | 3/2008 | Wells |
| 2001/0050082 A1 | 12/2001 | Chrisopher |
| 2003/0051734 A1 * | 3/2003 | Brain ............... 128/207.15 |
| 2004/0020491 A1 | 2/2004 | Fortuna |
| 2004/0079364 A1 | 4/2004 | Christopher |
| 2005/0016529 A1 | 1/2005 | Cook |
| 2005/0051173 A1 | 3/2005 | Brain |
| 2005/0139220 A1 | 6/2005 | Christopher |
| 2006/0027238 A1 | 2/2006 | Lin |
| 2006/0076021 A1 | 4/2006 | Chang |
| 2006/0180156 A1 | 8/2006 | Baska |
| 2006/0207597 A1 | 9/2006 | Wright |
| 2007/0028923 A1 | 2/2007 | Souris et al. |
| 2007/0102001 A1 | 5/2007 | Brain |
| 2007/0137651 A1 | 6/2007 | Glassenberg et al. |
| 2007/0246050 A1 | 10/2007 | Parikh et al. |
| 2008/0078398 A1 | 4/2008 | Cook |

FOREIGN PATENT DOCUMENTS

| | | |
|---|---|---|
| GB | 2323289 | 9/1998 |
| GB | 2357437 | 6/2001 |
| GB | 2374289 | 10/2002 |
| GB | 2374289 A | 10/2002 |
| WO | WO 00/20062 | 4/2000 |

OTHER PUBLICATIONS

"Ambu Product Information," Ambu A/S, 2007, pp. 1-18, Denmark.

"Intersurgical Complete Respiratory Systems," http://www.intersurgical.com/productscatalog/choosegroup.aspx?cm..., printed on Apr. 11, 2007, one page.

"LMA Airway Instruction Manual," The Laryngeal Mask Company Limited, www.lmana.com/docs/LMA_Airways_Manual.pdf, 2005, pp. 1-23.

International Search Report, International Patent Application No. PCT/US2008/060425, mailed Sep. 29, 2008, 11 pages.

* cited by examiner

LARYNGEAL MASK

CROSS-REFERENCE TO RELATED APPLICATIONS

This is a continuation-in-part of U.S. patent application Ser. No. 09/829,157, filed Apr. 9, 2001, and issued as U.S. Pat. No. 6,705,321, which is a continuation-in-part of U.S. patent application Ser. No. 09/179,928, filed on Oct. 27, 1998, and issued as U.S. Pat. No. 6,422,239, which is a divisional of U.S. patent application Ser. No. 08/843,631, filed on Apr. 10, 1997, and issued as U.S. Pat. No. 5,937,860.

STATEMENT REGARDING FEDERALLY SPONSORED RESEARCH OR DEVELOPMENT

Not applicable.

BACKGROUND OF THE INVENTION

This invention relates to an artificial airway device designed to facilitate lung ventilation and the insertion of endotracheal tubes or related medical instruments into the laryngeal opening of an unconscious patient, and more specifically to a laryngeal mask designed to be placed within the oropharynx region over the laryngeal opening to conceal the circumference of the laryngeal opening against the aspiration of regurgitated gastric content and provide a direct pathway from a perimeter exterior to the oral cavity to the laryngeal opening.

In general, laryngeal masks allowing for both rapid lung ventilation and the insertion of medical instruments and tubes into the laryngeal openings of patients have been described in patents such as U.S. Pat. No. 4,509,514 to Brain. Consisting of two essential parts, a breathing tube and an inflatable mask, these devices are inserted blindly into a patient's throat, and when properly positioned, terminate at the laryngeal opening. Generally, a seal is then formed around the circumference of the laryngeal opening by the inflation of a ring-like structure located on the front of the mask. Inflation of the ring exerts pressure against both the front and rear portions of the oropharynx, securing the device in place such that the laryngeal opening is positioned within the cavity in the mask face. Extending from a point external to the oral cavity, the flexible breathing tube terminates within the cavity, which is aligned axially with the laryngeal opening. The positioning of the flexible breathing tube allows the passage of small diameter endotracheal tubes or related medical instruments into the laryngeal opening, in addition to allowing for lung ventilation.

Current laryngeal masks have several drawbacks in the area of placement, lung ventilation, and endotracheal intubation. For example, during insertion and positioning, the flexible nature of the deflated ring structure and surrounding mask allows the distal end of the mask to bend back on itself, making placement difficult. Also, once installed, the current mask designs fail to exert sufficient pressure against the larynx necessary to maintain proper positioning during intubation and ventilation. This is due to the variations in the anatomy of the oropharynx region and the curvature of the device itself. Further, during lung ventilation it is possible for the tip of the epiglottis to become lodged in the distal lumen of the flexible breathing tube, which inhibits the passage of air or endo-tracheal tubes through the tube. This problem is often overcome by the placement of a series of band structures at the entrance of the distal lumen that prevent the epiglottis from entering the breathing tube. However, these band structures severely restrict the size of the endo-tracheal tubes or related medical devices that may be passed through the flexible breathing tube. Moreover, after insertion of an endotracheal tube or related medical device, it becomes difficult to remove the laryngeal mask from the patient's oropharynx without dislodging or accidentally extracting the endo-tracheal tube or medical device along with the laryngeal mask.

Accordingly a laryngeal mask that provides generally the same function as described above is needed that allows a more secure insertion and airtight placement, allows the unrestricted passage of large diameter endo-tracheal tubes directly into the laryngeal opening, and provides alternative airways.

SUMMARY OF THE INVENTION

Briefly stated, a laryngeal mask of the type used to facilitate lung ventilation and the insertion of endotracheal tubes or related medical instruments through a patient's laryngeal opening as used during general anesthesia, intensive care, or critical patient care is provided that includes an inflatable positioning shield formed to fit within the patient's oropharynx, the positioning shield having an inflatable, hollow peripheral portion, and a posterior base in fluid communication with the peripheral portion, a shield recess formed after inflation of the peripheral portion, and a rear portion formed between the posterior base and the peripheral portion after inflation of the peripheral portion, wherein the posterior base has a recessed front portion, and a respiratory tube having a proximal end lumen, a curved tubular body of sufficient size to permit passage of endo-tracheal tubes or related medical instruments therethrough, and a distal end passing through and secured to the rear portion of the positioning shield, the distal end terminating at a distal lumen, the distal lumen passing through and secured to the rear portion of the positioning shield such that tubes and instruments passing through the respiratory tube will be directed into the laryngeal opening;

In a second aspect of the invention, the above-described laryngeal mask comprised of a respiratory tube that has an elliptical cross-section, where the cross-section is perpendicular to the longitudinal axis of the tube;

In a third aspect of the invention, the above-described laryngeal mask comprises a distal lumen that has an elliptical cross-section, where the cross-section is perpendicular to the longitudinal axis of the tube;

In a fourth aspect of the invention, the laryngeal mask comprises a distal lumen that has an upper portion and a lower portion, wherein the upper portion and the lower portion have about the same diameter, the diameter of the upper portion and the lower portion being smaller than the diameter of the proximal end lumen;

In a fifth aspect of the invention, the above described laryngeal mask comprises a distal lumen that has an upper portion and a lower portion, wherein the upper portion and the lower portion have about the same diameter, the diameter of the upper portion and the lower portion being smaller than the diameter of the proximal end lumen, wherein the distal lumen is sufficiently pliable such that it opens upon the assertion of pressure thereon and returns to its original shape when the pressure is released;

In a sixth aspect of the invention, the above described laryngeal mask comprises a distal lumen that has an upper portion and a lower portion, wherein the upper portion has a diameter that is different from the diameter of the lower portion;

In a seventh aspect of the invention, the above-described laryngeal mask further comprises at least one raised horizontal runner that is a continuous extension of the posterior base;

In an eighth aspect of the invention, a laryngeal mask of the type used to facilitate lung ventilation and insertion of endo-tracheal tubes or related medical instruments through a patient's laryngeal opening as used during general anesthia, intensive care, or critical patient care is provided that includes an inflatable positioning shield formed to fit within the anatomical structures of the oropharynx region when inflated, the positioning shield enclosing the laryngeal opening within a recessed front, and having an inflatable, hollow peripheral portion, the recessed front being sufficiently pliable to cup the patient's tracheal after inflation of the positioning shield, and a respiratory tube having a proximal end lumen, a curved tubular body having an elliptical cross-section, and being sufficiently radially deformable to permit passage of endo-tracheal tubes or related medical instruments therethrough, and a distal end passing through and secured in an airtight manner to the rear portion of the positioning shield, terminating at a distal lumen within the rear portion of the positioning shield so as to be aligned axially with the laryngeal opening upon insertion into the oropharynx, wherein the cross-section is perpendicular to the longitudinal axis of the tube;

In a ninth aspect of the invention, a laryngeal mask of the type used to facilitate lung ventilation and the insertion of endo-tracheal tubes or related medical instruments through a patient's laryngeal opening as used during general anesthesia, intensive care, or critical patient care is provided that comprises an inflatable positioning shield curved to fit within the patient's oropharynx, the positioning shield having an inflatable, hollow peripheral portion, a posterior base in fluid communication with the peripheral portion, a shield recess formed after inflation of the peripheral portion, and a rear portion formed between the posterior base and the peripheral portion after inflation of the peripheral portion, wherein the posterior base has a recessed front portion, the recessed front portion being sufficiently pliable to cup the patient's trachea after inflation of the positioning shield, thereby limiting lateral movement of the laryngeal mask, and a respiratory tube having a proximal end lumen, a curved tubular body of sufficient size to permit the passage of endo-tracheal tubes and related medical instruments therethrough, and a distal end passing through and secured to the rear portion of the positioning shield, the distal end terminating at a distal lumen, wherein the distal lumen passes through and is secured to the rear portion of the positioning shield such that tubes or related medical instruments passing through the respiratory tube will be directed into the laryngeal opening, wherein the recessed front portion of the posterior base comprises at least one raised horizontal runner that is a continuous extension of the posterior base, and wherein the distal lumen comprises an upper portion and a lower portion, wherein the upper portion and the lower portion have about the same diameter, the diameter of the upper portion and the lower portion being smaller than the diameter of the proximal end lumen;

In a tenth aspect of the invention, a laryngeal mask of the type used to facilitate lung ventilation and the insertion of endo-tracheal tubes or related medical instruments through a patent's laryngeal opening as used during general anesthesia, intensive care, or critical patient care is provided that comprises an inflatable positioning shield formed to fit within a patient's oropharynx, the positioning shield having an inflatable, hollow peripheral portion, a posterior base in fluid communication with the peripheral portion, a shield recess formed after inflation of the peripheral portion, and a rear portion formed between the posterior base and the peripheral portion after inflation of the peripheral portion, wherein the posterior base has a recessed front portion that is sufficiently pliable to cup the patient's trachea after inflation of the positioning shield and a respiratory tube having a proximal end lumen, a curved tubular body of sufficient size to permit passage of endo-tracheal tubes and related medical instruments therethrough, and a distal end passing through and secured to the rear portion of the positioning shield, the distal end terminating at a distal lumen, the distal lumen passing through and secured to the rear portion of the inflatable positioning shield such that tubes or other related medical instruments passing through the respiratory tube will be directed into the laryngeal opening, wherein the recessed front portion of the posterior base comprises at least one raised horizontal runner that is a continuous extension of the posterior base, wherein the distal lumen comprises an upper portion and a lower portion wherein the upper portion and the lower portion, have about the same diameter, the diameter of the upper portion and the lower portion being smaller than the diameter of the proximal end lumen, and wherein the distal lumen is sufficiently pliable such that it opens upon the assertion of pressure thereon and returns to its original shape when the pressure is released;

In an eleventh aspect of the invention, a laryngeal mask of the type used to facilitate lung ventilation and the insertion of endo-tracheal tubes or related medical instruments through a patient's laryngeal opening as used during general anesthesia, intensive care, or critical patient care is provided that comprises an inflatable positioning shield formed to fit within a patient's oropharynx, the positioning shield having an inflatable, hollow peripheral portion, a posterior base in fluid communication with the peripheral portion, a shield recess formed after inflation of the peripheral portion and a rear portion formed between the posterior base and the peripheral portion after inflation of the peripheral portion, wherein the posterior base has a recessed front portion, the recessed front portion being sufficiently pliable to cup the patient's trachea after inflation of the positioning shield, and a respiratory tube having a proximal end lumen, a curved tubular body of sufficient size to permit passage of endo-tracheal tubes and related medical instruments therethrough, and a distal end passing through and secured to the rear portion of the positioning shield, the distal end terminating at a distal lumen, the distal lumen passing through and secured to the rear portion of the positioning shield such that tubes or related medical instruments passing through the respiratory tube will be directed into the laryngeal opening, wherein the distal lumen comprises an upper portion and a lower portion, the upper portion having a diameter that is different from the diameter of the lower portion;

In a twelfth aspect of the invention, a laryngeal mask of the type used to facilitate lung ventilation and the insertion of endo-tracheal tubes or related medical instruments through a patient's laryngeal opening as used during general anesthesia, intensive care, or critical patient care is provided that comprises an inflatable positioning shield formed to fit within a patient's oropharynx, the positioning shield having an inflatable, hollow peripheral portion, a posterior base in fluid communication with the peripheral portion, a shield recess formed after inflation of the peripheral portion and a rear portion formed between the posterior base and the peripheral portion after inflation of the peripheral portion, wherein the posterior base has a recessed front portion, the recessed front portion being sufficiently pliable to cup the patient's trachea after inflation of the positioning shield, thereby limiting lateral movement of the laryngeal mask, and a respiratory tube having a proximal end lumen a curved tubular body of sufficient size to permit passage of endo-tracheal tubes and related medical instruments therethrough, and a distal end passing through and secured to the rear portion of the positioning shield, the distal end terminating at a distal lumen, the distal lumen passing through and secured to the rear portion of the positioning shield such that tubes and related medical instruments passing through the respiratory tube will be directed into the laryngeal opening, wherein the distal lumen comprises an upper portion and a lower portion, wherein the upper portion has a larger diameter than the diameter of the lower portion, and wherein the distal end of the respiratory tube comprises at least one lumen, the at least one lumen having a diameter that is smaller than the diameter of the proximal end lumen; and In a thirteenth aspect of the invention, a laryngeal mask of the type used to facilitate lung ventilation and the insertion of endo-tracheal tubes or related medical instruments through a patient's laryngeal opening as used during general anesthesia, intensive care, or critical patient care is provided that comprises an inflatable positioning shield formed to fit within a patient's oropharynx, said positioning shield having an inflatable, hollow peripheral portion, a pliable base in fluid communication with the peripheral portion, a shield recess formed after inflation of the peripheral portion and a rear portion formed between the posterior base and the peripheral portion after inflation of the peripheral portion, wherein the posterior base has a recessed front portion that is sufficiently pliable to cup the patient's trachea after inflation of the positioning shield and a respiratory tube having a proximal end lumen, a curved tubular body of sufficient size to permit passage of endo-tracheal tubes and related medical instruments therethrough, and a distal end passing through and secured to the rear portion of the positioning shield, the distal end terminating at a distal lumen, the distal lumen passing through and secured to the rear portion of the positioning shield such that tubes and related medical instruments passing through the respiratory tube will be directed into the laryngeal opening, wherein the distal lumen comprises an upper portion and a lower portion, wherein the upper portion has a larger diameter than the lower portion, wherein the distal end of the respiratory tube comprises at least one lumen, the at least one lumen having a diameter that is smaller than the diameter of the proximal end lumen, and wherein the recessed front portion of the posterior base comprises at least one horizontal runner that is a continuous extension of the posterior base.

BRIEF DESCRIPTION OF THE DRAWINGS

Corresponding reference numerals indicate corresponding parts throughout the several figures of the drawings.

DESCRIPTION OF THE PREFERRED EMBODIMENTS

The following detailed description illustrates the invention by way of example and not by way of limitation. The description will clearly enable one skilled in art to make and use the invention, describe several embodiments, adaptations, variations, alternatives, and uses of the invention including what is believed to be the best mode of carrying out the invention.

Figure 1:
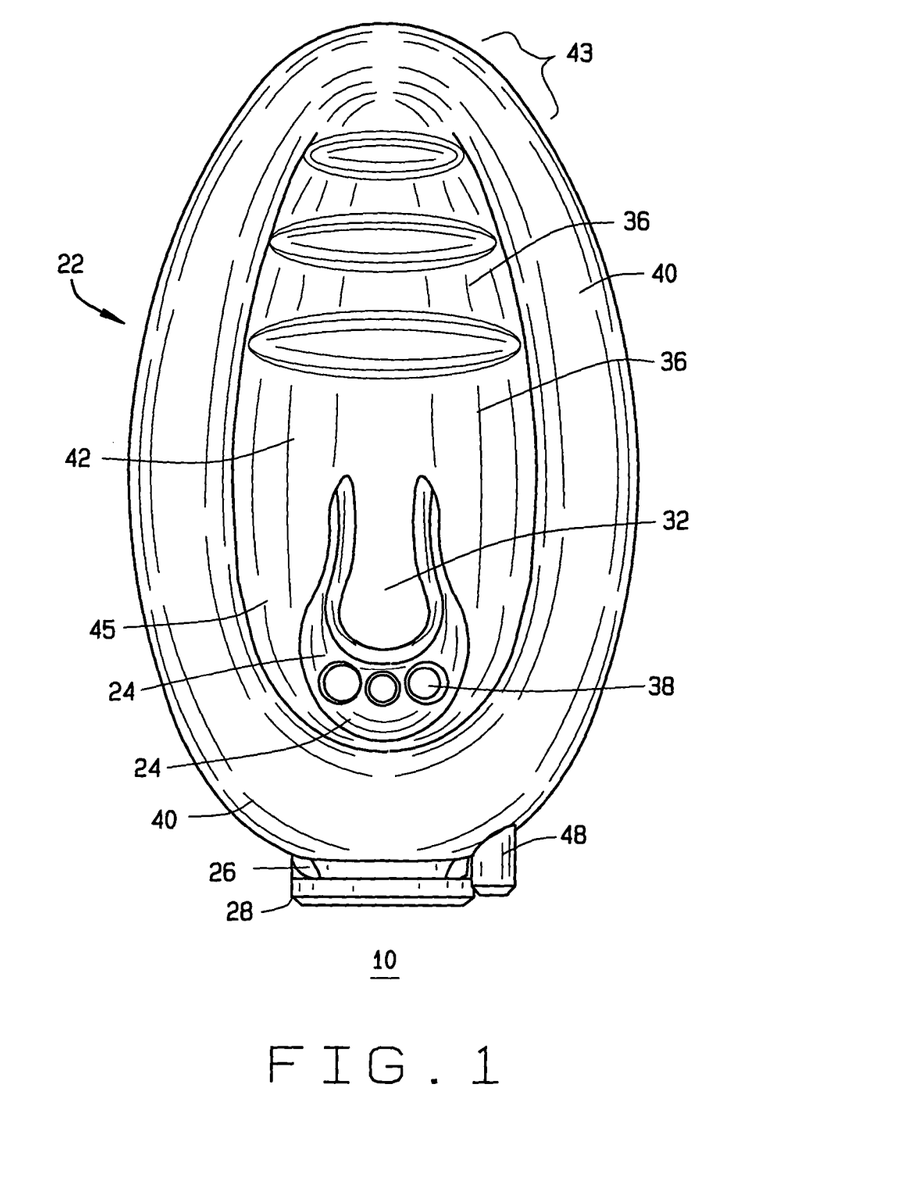
FIG. 1 is a top view of an embodiment of the laryngeal mask of the invention illustrating the flexible breathing tube and the inflatable positioning shield.
Figure 2:
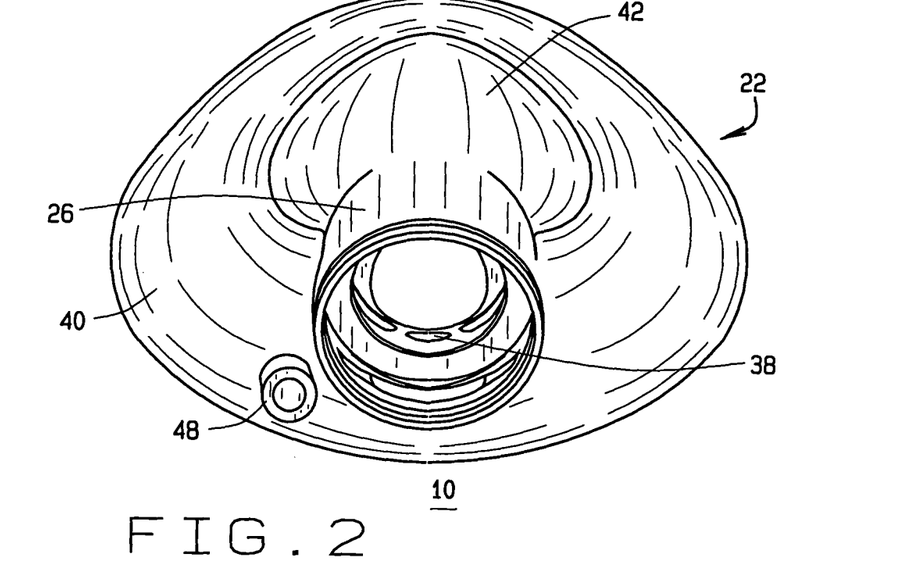
FIG. 2 is a bottom plan view of one embodiment of the laryngeal mask of the invention.
Figure 3:
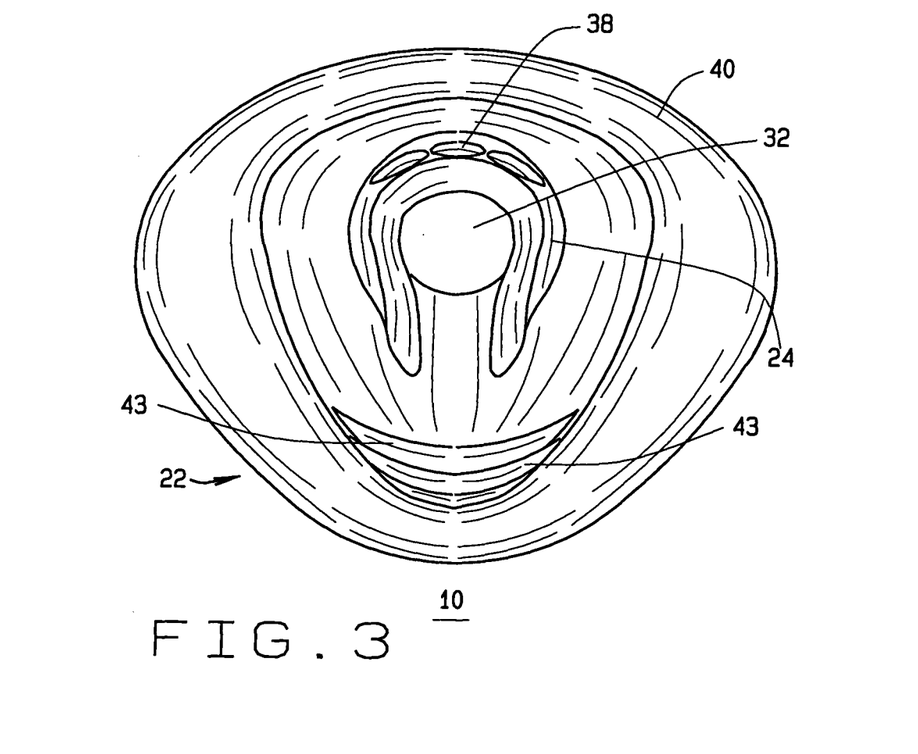
FIG. 3 is a front plan view of one embodiment of the laryngeal mask of the invention.
Figure 4:
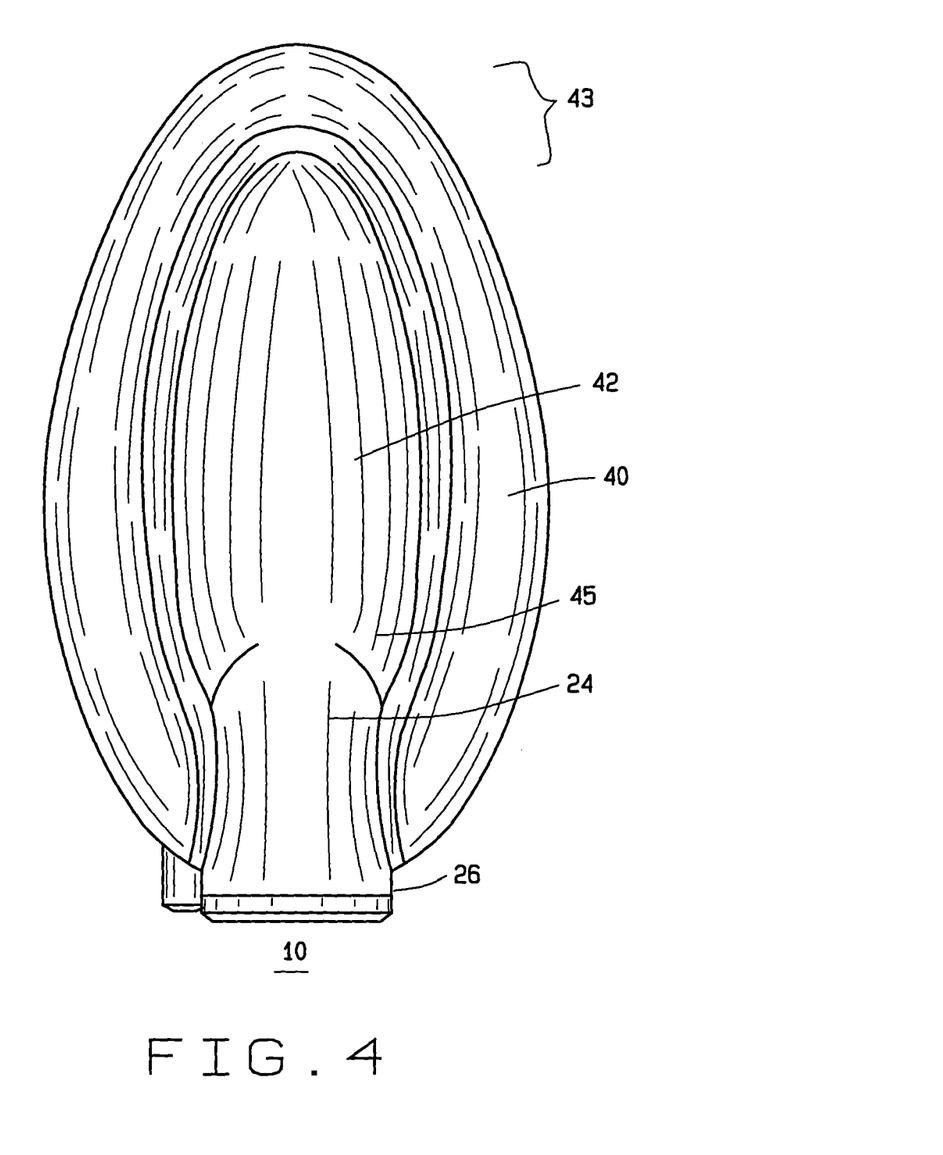
FIG. 4 is a bottom view of the inflatable positioning shield of the invention.
Figure 5:
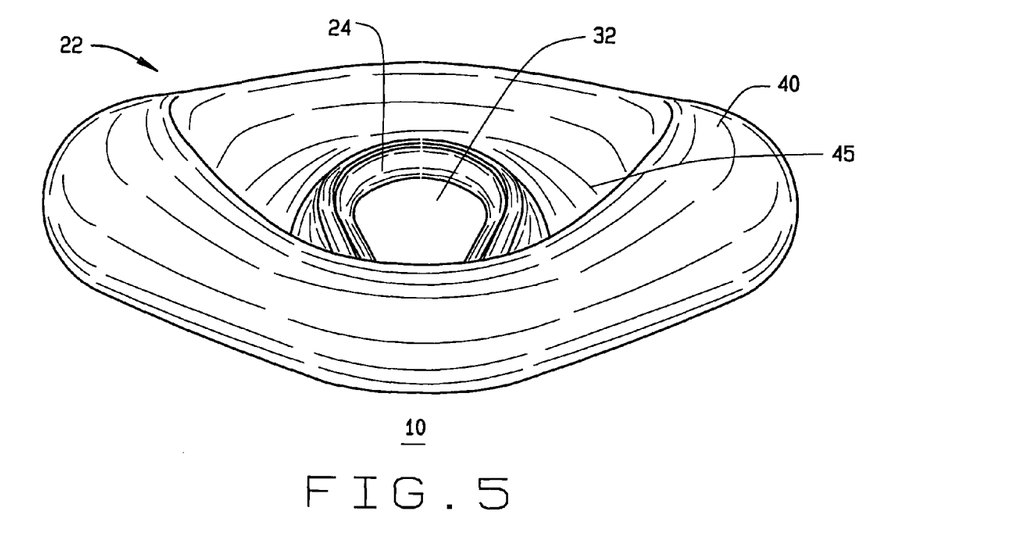
FIG. 5 is a front view of the inflatable positioning shield after inflation, illustrating the recessed front portion of the positioning shield and the unobstructed distal lumen of the flexible breathing tube.
Figure 6:
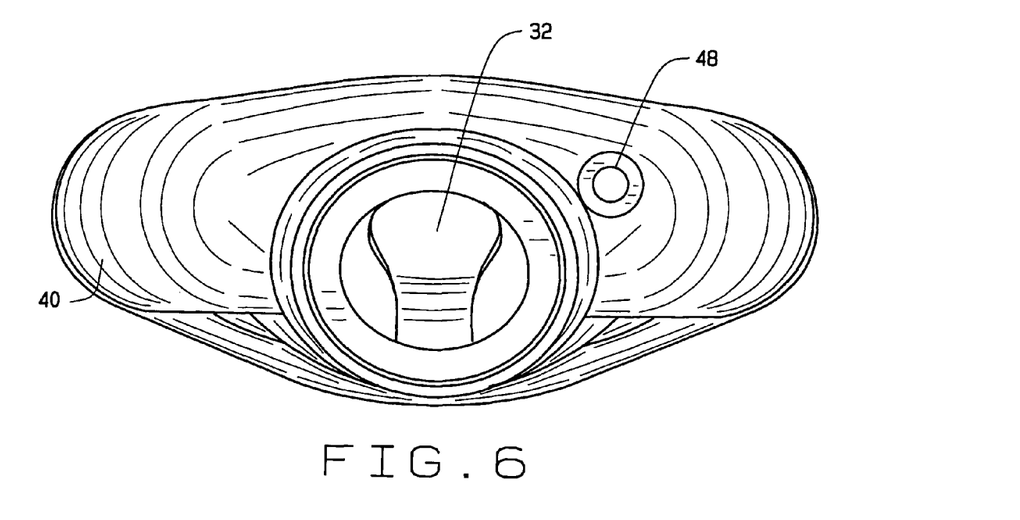
FIG. 6 is a rear view of the inflatable positioning shield after inflation, with the flexible breathing tube removed.

Referring to the drawings, and particularly FIGS. 1-3, a new and useful laryngeal mask 10 has been invented that provides generally the same function as current laryngeal masks, while avoiding some of the problems associated with their use. Specifically, the laryngeal masks 10 of the invention can be more securely and certainly inserted and removed, permitting the unrestricted passage of large diameter endotracheal tubes directly to the laryngeal opening, and providing alternate airways to prevent blockage of the breathing tube during patient ventilation. In accordance with the invention, a laryngeal mask 10 is provided that comprises an inflatable positioning shield 22 secured to distal end 24 of respiratory tube 26, forming a smooth arcuate curve. Inflatable positioning shield 22 is formed to fit within a patient's oropharynx. The positioning shield 22 of the invention has an inflatable, hollow peripheral portion 40, a pliable base 42 in fluid communication with the peripheral portion 40, a shield recess 36 formed after inflation of peripheral portion 40, and a rear portion 45 formed between posterior base 42 and the peripheral portion 40 after inflation of the peripheral portion 40. Posterior base 42 has a recessed front portion 43 to facilitate insertion and removal of inflatable positioning shield 22 into the patient's airway. Generally, and in one embodiment of the invention, posterior base 42 is comprised a material that imparts pliability thereto.

Respiratory rube 26 comprises a proximal end lumen 30, a curved tubular body of sufficient size to permit passage of endotracheal tubes or related medial instruments therethrough, and a distal end 24 passing through and secured to the rear portion 45 of the positioning shield. Distal end 24 of respiratory tube 26 terminates at a distal lumen 32, which passes through the peripheral portion 40 of the positioning shield 22 and is secured to the rear portion 45 of the positioning shield such that tubes and instruments passing though respiratory tube 26 will be directed into the laryngeal opening. Respiratory tube 26 may have any cross-section shape, provided that medical instruments are not prevented from passing therethrough. In one embodiment, respiratory tube 26 has an oval cross-sectional shape, where the cross-section is perpendicular to the longitudinal axis of the tube 26. In another embodiment, respiratory tube 26 has a circular cross-sectional shape, where the cross-section is perpendicular to the longitudinal axis of the tube 26.

Inflatable positioning shield 22 comprises an inflatable, hollow peripheral portion 40. Inflation of positioning shield 22 is accomplished by means of any conventional inflation device. These devices are readily available and known in the art. Generally, and with reference to FIG. 1, peripheral portion 40 comprises a means for allowing inflation 48 thereof that is generally located in a proximal area of peripheral portion 40, near distal end 24 of respiratory tube 26. However, the means for allowing inflation 48 may be in any convenient location, provided that inflation of peripheral portion 40 after insertion into a patient's airway is not hindered. The means for allowing inflation is generally a small aperture, which may be circular, oval or slot-shaped.

Peripheral portion 40 may be of any shape, so long as the shape does not prevent insertion of the positioning shield 22 into the patient's oropharynx. In a preferred embodiment of the invention, peripheral portion 40 forms an ovoid, or wedge shape when inflated to conform to the approximate available space in the oropharynx region. Posterior base 42 is secured in an airtight manner in fluid communication with peripheral portion 40 of inflatable positioning shield 22. Posterior base 42 forms an elongated and tapered hemisphere. Upon inflation of positioning shield 22, shield recess 36 is formed. Posterior base 42 comprises recessed front portion 43, which is sufficiently pliable to cup the patient's trachea after inflation of positioning shield 22, thereby limiting lateral movement of laryngeal mask 10.

Hollow inflatable positioning shield 22 is secured to distal end 24 of respiratory tube 26. Generally, and in one embodiment of the invention, respiratory tube 26 is comprised of a material that imparts flexibility thereto. Respiratory tube 26 may be manufactured using any material this is sufficiently flexible to allow insertion of the tube into the patient's airway. In one embodiment, respiratory tube 26 comprises a flexible silicone-rubber polymer. In another embodiment, respiratory tube 26 comprises polyvinylchloride. Generally, respiratory tube 26 is capable of spreading radially, and can accommodate the passage of endotracheal tubes and related medical devices up to 8.0 French in the diameter. However, it is contemplated that respiratory tube 26 can accommodate medical devices having larger diameters. However, it should be noted that respiratory tube 26 need not be flexible in accordance with the invention.

The length of respiratory tube 26 is such that when laryngeal mask 10 is properly positioned for use in the oropharynx, proximal or attachment end 28 of respiratory tube 26 is located exterior to the oral cavity. As is readily known in the art, respiratory tube 26 may comprise one or more lumens therein. Attachment end 28 of respiratory tube 26 terminates in unobstructed proximal lumen 30, providing a direct pathway to respiratory tube 26 to distal end 24 and distal lumen 32. In an alternative embodiment, attachment end 28 may be fitted with adaptors or connectors that are suitable for connection to the variety of medical devices, for example lung ventilation machine.

Figure 7:
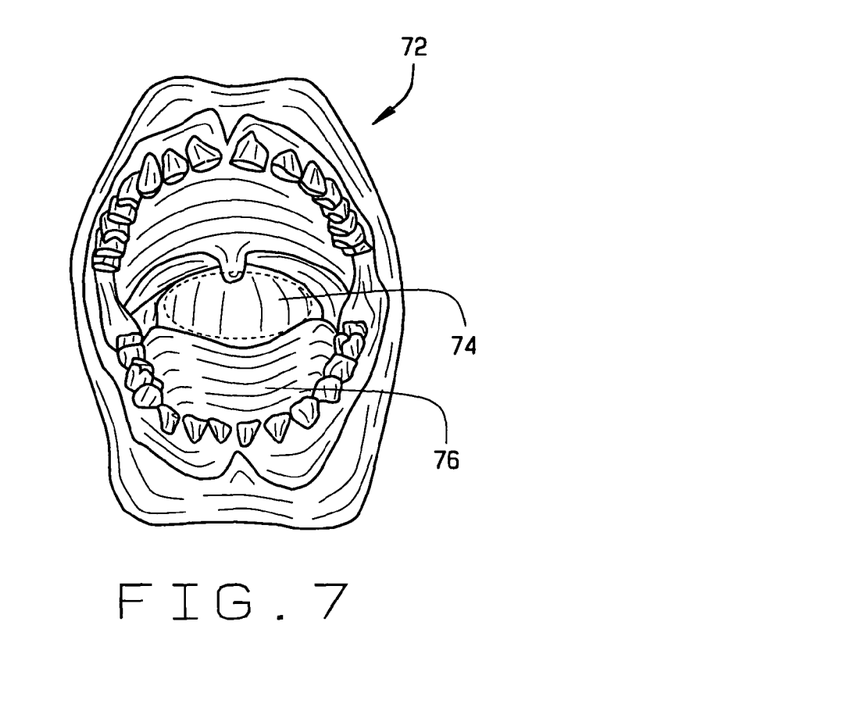
FIG. 7 is an illustration of a patient's oral cavity, illustrating the elliptical shape of the opening into the laryngeal region.

Respiratory tube 26 may be of any shape, provided that the shape does not inhibit the passage of endotracheal tubes and related medical devices into the laryngeal opening. In one embodiment of the invention, attachment end 28 of respiratory tube 26 has an elliptical cross-section, approximating the shape of the human throat as shown in FIG. 7. The cross-sections referred to herein and through this specification are perpendicular to the longitudinal axis of the component referred to.

Figure 8:
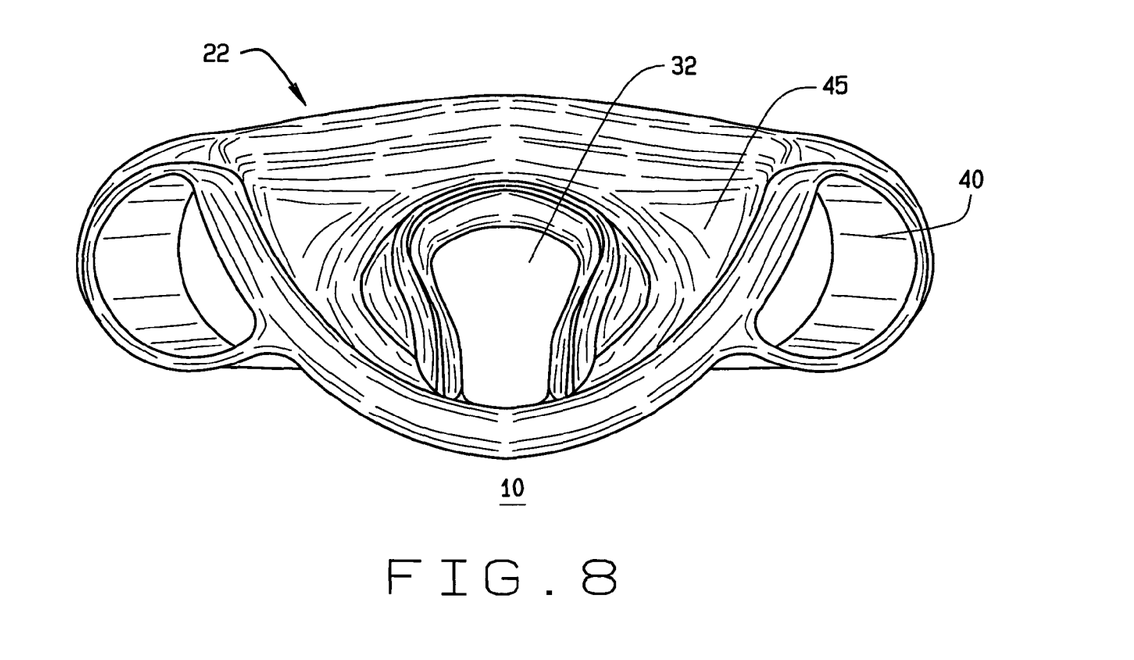
FIG. 8 is a sectional view of one embodiment of a laryngeal mask of the invention, illustrating the rear portion of the positioning shield, and the key-hole shape unobstructed distal lumen of the flexible breathing tube.

Distal end 24 is a continuous portion of respiratory tube 26, which has passed through the rear portion 45 of inflatable positioning shield 22. Rear portion 45 is formed between posterior base 42 and peripheral portion 40 after inflation of peripheral portion 40. Distal end terminates at an angle to its length forming the elongated distal lumen 32, which is open to the interior of shield recess 36. As shown in FIG. 8, the distal lumen 32 passes through the peripheral portion 40 of the positioning shield 22.

Respiratory tube 26 is comprised of a curved tubular body of sufficient size to permit the passage of endotracheal tubes and related medical instruments therethrough. In one embodiment of the invention, respiratory tube 26 and positioning shield 22 are pre-curved along about the same arcuate curve such that minimal bending of respiratory tube 26 is required during positioning of laryngeal mask 10 around the laryngeal opening. Generally, and in one embodiment of the invention, respiratory tube 26 is composed of a material with a low coefficient of friction to facilitate the delivery of endotracheal tubes and related medical instruments through respiratory tube 26 outside of the patient's laryngeal opening. Respiratory tube 26 generally comprises a material that allows it to deform radially to allow passage of endotracheal tubes and related medical instruments having large circular cross-sections, and return to its original cross-sectional shape upon the removal of the instruments. In specific embodiments, respiratory tube 26 returns to its original elliptical cross-sectional shape upon the removal of the instruments.

In one embodiment of the invention, at least one lumen 38 perforates distal end 24 to provide alternate airways in the event that that distal lumen 32 becomes obstructed during patient lung ventilation. Lumens 38 have diameters that are smaller than the diameter of distal lumen 32 and generally provide a ventilation alternative to distal lumen 32 and prevent the formation of a pressure differential between shield recess 36 and respiratory tube 26. Absent this differential, any object obstructing the distal lumen 32 will not become inextricably lodged within distal end 24. Lumens 38 may be any shape including, but not limited to circular, oval and slot-shaped.

Laryngeal masks 10 of the invention comprise an inflatable positioning shield 22 that includes recessed front portion 43. Recessed front portion 43 is generally made of the same material as the other portions of laryngeal mask 10. Generally, recessed front portion 43 comprises a material that makes it pliable. It is preferred that it comprises a material that makes it sufficiently pliable to cup the patient's trachea after inflation of positioning shield 22. This inhibits lateral movement of laryngeal mask 10 during use. Suitable materials that will impart pliability to recessed front portion 43 include polyvinylchloride ("PVC") and silicone. It should be noted, however, that other materials may be used that impart pliability that are within the scope of this invention including, but not limited to polyurethane, EVA, TPE, polyether block amide, or the like.

It should also be noted that recessed front portion 43 may not comprise a material that imparts pliability. Recessed front portion 43 may be rigid in accordance with the invention.

Figure 9:
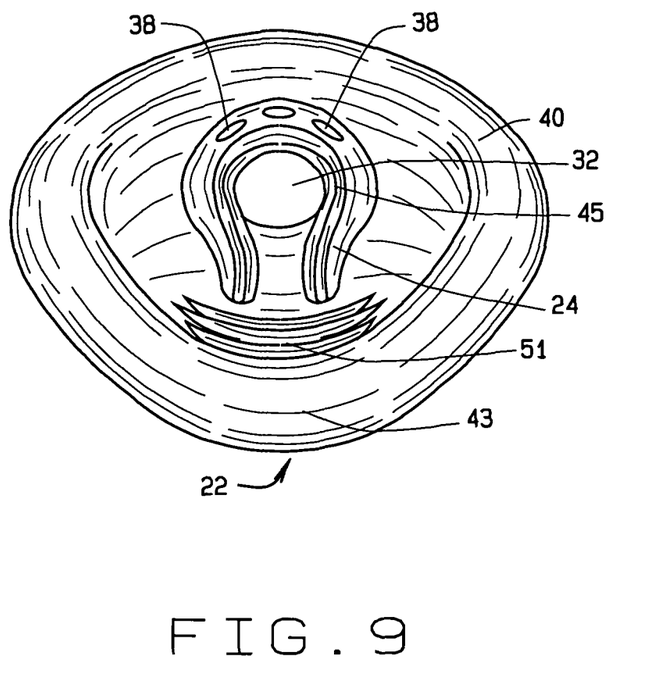
FIG. 9 is a top plan view of the inflatable positioning shield after inflation, illustrating the recessed front portion of the positioning shield, the key-hole shaped unobstructed distal lumen of the flexible breathing tube, the raised horizontal runners and the small diameter lumens.
Figures 10, 11, 12:
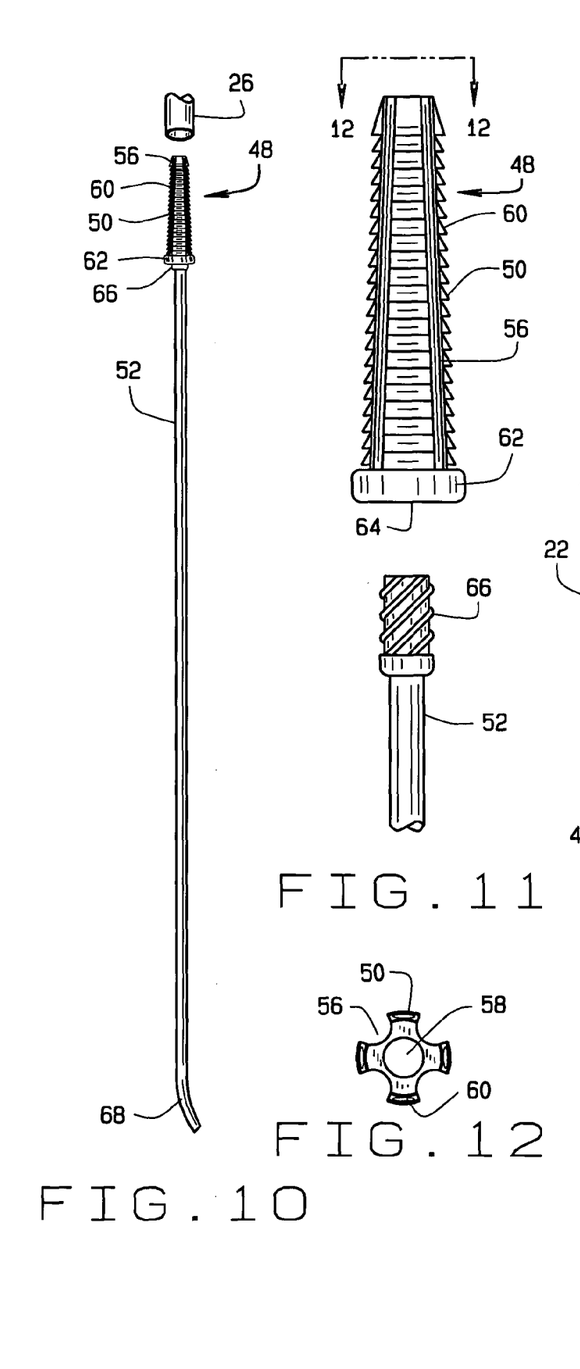
FIG. 10 is a plan view of the endotracheal tube retainer, illustrating the end cap.
FIG. 11 is a plan view of the endotracheal tube retainer, illustrating the separation of the tube retainer body from the connection adapter.
FIG. 12 is a front view of the distal end of the connection adaptors, illustrating the airflow grooves.

In one embodiment of the invention, and with reference to FIG. 9, recessed front 43 portion of inflatable positioning shield 22 comprises at least one support member 51 that is adapted to stabilize posterior base 42 of inflatable positioning shield 22 or that is adapted to inhibit gastric aspirate, or other foreign matter, from entering the shield recess 36. Support member 51 may be any member that is adapted to impart stability or rigidity to posterior base 42. Support member 51 may also be any member that is adapted to inhibit foreign matter from entering the shield recess 36. In one embodiment of the invention, the support member is a raised horizontal runner that is a continuous extension of posterior base 42. In a more specific embodiment of the invention, recessed front 43 portion of inflatable positioning shield 22 includes a plurality of raised runners 51.

In a specific embodiment of the invention, laryngeal mask 10 does not comprise an inflatable positioning shield that includes a recessed front portion.

In accordance with the invention, distal end 24 terminates at an angle to its length, forming distal lumen 32 that is open to the interior of shield recess 36. In one embodiment, distal lumen 32 has about the same cross-sectional shape as the respiratory tube 26. Accordingly, and in one embodiment of the invention, distal lumen 32 has an elliptical cross-section. In another embodiment of the invention, distal lumen 32 has a diameter that is smaller than the diameter of proximal end lumen 30. It is believed that the shape of distal lumen 32 forces any endotracheal tubes or related medical instruments inserted toward the center of distal lumen 32 and in an upward direction, thereby leaving space for the insertion and use of other medical instruments that have been inserted into the respiratory tube. It is also believed that the epiglottis is forced onto distal end 24 of respiratory tube 26, allowing any medical instruments inserted into respiratory tube 26 direct access to the oropharynx. Therefore, manual movement of the epiglottis is not required as with current laryngeal masks and methods of using such.

In one embodiment of the invention, and with reference to FIGS. 1 and 3, distal lumen 32 comprises an upper portion and a lower portion, the upper portion having a larger diameter than the lower portion. This shape is generally referred to as a keyhole shape.

In another specific embodiment of the invention, distal lumen 32 comprises an upper and lower portion, which both have about the same diameter, which is smaller than the diameter of proximal end lumen 30 and distal lumen 32. In this embodiment, distal lumen 32 is slot-shaped. In a more specific embodiment of the invention, distal lumen 32 is also sufficiently pliable such that it opens upon assertion of pressure thereon and returns to its original shape when the pressure is released. Accordingly, endotracheal tubes and other related medical devices could be safely inserted into laryngeal opening by applying pressure onto distal lumen 32.

During use, laryngeal mask 10 is inserted through the oral cavity with peripheral portion 40 fully deflated. The smooth arcuate curve of laryngeal mask 10, including respiratory tube 26 and positioning shield 22, ensures proper positioning of laryngeal mask 10 within the anatomy surrounding the laryngeal opening. Upon proper positioning, as determined by resistance to further forward motion, peripheral portion 40 is inflated. When fully inflated, peripheral portion 40 exerts sufficient pressure against the structures of the oropharynx, permitting positive lung ventilation to be performed, and allowing endotracheal tubes or related medical instruments to be inserted through respiratory tube 26 and into distal lumen 32. The inserted instruments are thereby directly aligned for passage into the laryngeal opening.

Removal of laryngeal mask 10 is normally the reverse of the insertion procedure described above. In some situations however, it is desired to remove laryngeal mask 10 without simultaneously removing or dislodging inserted endotracheal tubes or related medical instruments or devices passing through respiratory tube. You will find generally to FIGS. 10 through 15, removal of laryngeal mask 10 under some circumstances is facilitated by means of a tube retainer, shown generally at 48.

Figure 13:
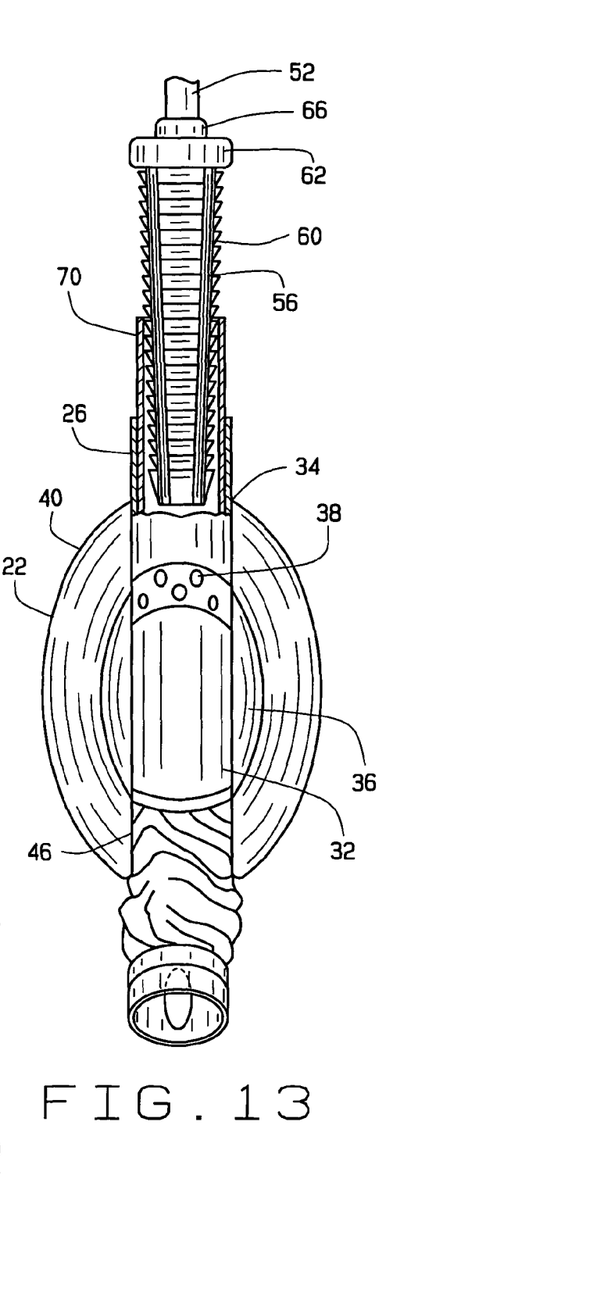
FIG. 13 is a plan view of the laryngeal mask of the invention during use, illustrating interaction with an endo-tracheal tube retainer.
Figure 14:
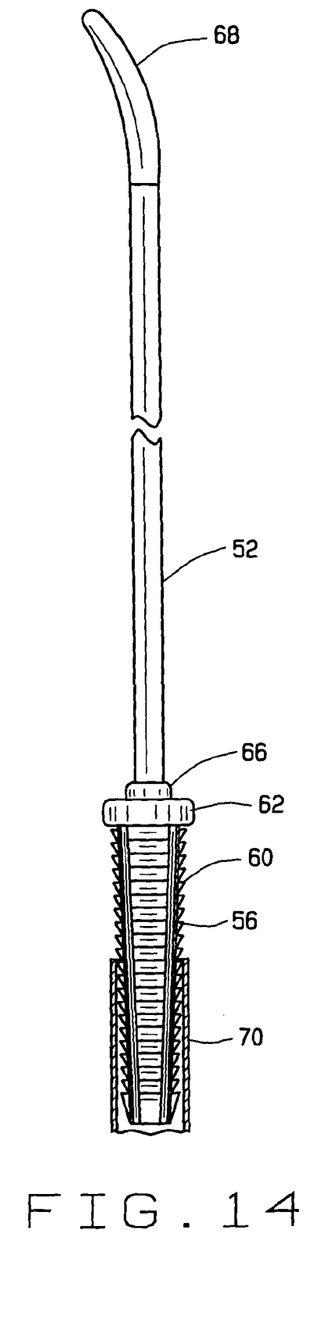
FIG. 14 is a plan view of an endo-tracheal tube retainer during use, illustrating proper positioning of the tube retainer.
Figure 15:
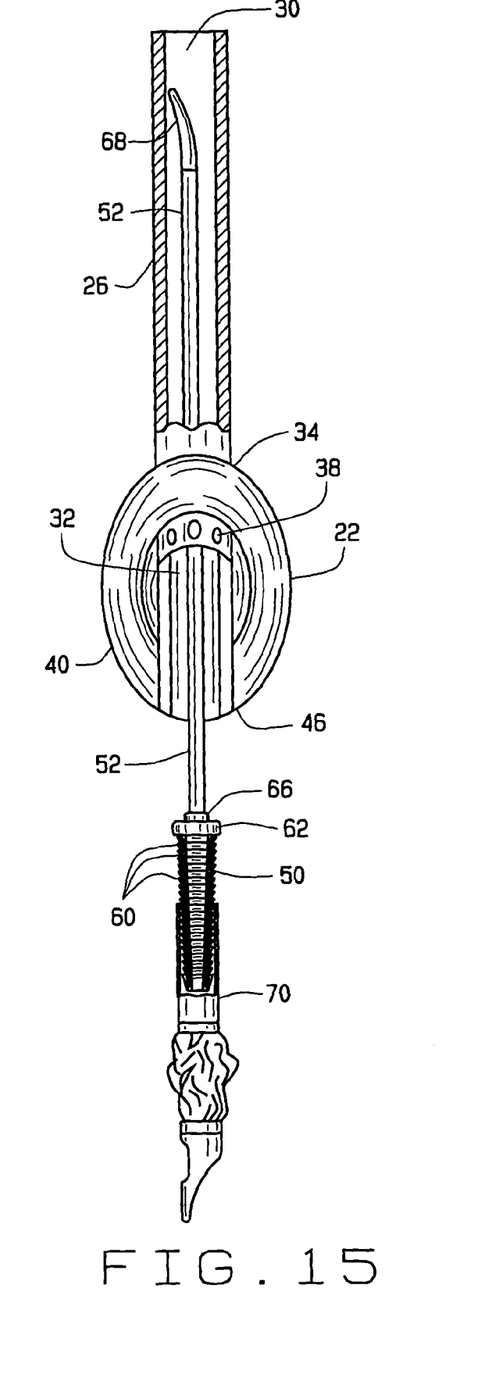
FIG. 15 is a plan view of the laryngeal mask during removal, illustrating the operation of the endotracheal tube retainer.

Tube retainer 48 comprises a connection adapter 50 and solid rod 52. In an alternate embodiment, tube retainer 48 additionally comprises end cap 68. Connection adapter 50 is composed of a soft semi-rigid material forming a truncated conical structure having at least one longitudinal ventilation groove 56. Ventilation groove 56 permits the passage of air around connection adapter 50 after insertion within an endotracheal tube, as shown in FIGS. 13-15. The exterior surface of connection adapter 50 between each ventilation groove 56 is threaded or grooved with thread 60. Each thread 60 is angled and shaped so as to facilitate insertion of connection adapter 50 into an endotracheal tube by means of a longitudinally directed force applied to adapter 50. Alternatively, adapter 50 may be screwed into place, and unscrewed, as desired. The conical nature of connection adapter 50 permits tube retainer 48 to fit securely within the opening of a variety of endotracheal tubes, generally ranging from standard size number 6 to standard size number 8 tubes. The present invention may be adapted as desired to accommodate larger or smaller tubes, or both, without departing from the scope of the current invention. As tube retainer 48 is inserted within the opening of an endotracheal tube, the increasing exterior diameter of connection adapter 50 prevents insertion beyond a certain point, limited by the interior diameter of the endotracheal tube.

Solid rod 52 is a semi-rigid, circular, cross-section rod, where the cross-section is perpendicular to the longitudinal axis of the rod. Again, all cross-sectional references herein are perpendicular to the longitudinal axis. The length of solid rod 52 is sufficient to traverse the distance between a point external to a patient's oral cavity and the laryngeal opening. During the insertion of the tube retainer within an endotracheal tube or related medical instrument, the end of solid rod 52 that is external to the oral cavity may consist of a softer end cap 68. Of course, rod 52 may be used separately as an intubating stylet for direct visualization by unscrewing adapter 50 from rod 52 and placing cap 68 into the trachea directly. It should be noted, that rod 52 is a solid rod. Soft cap 68 is designed and configured to reduce potential tracheal trauma when used as an intubating stylet.

FIGS. 13-15 illustrate the use of tube retainer 48 during removal of laryngeal mask 10. As described above, the use of a tube retainer prevents the displacement of any inserted endotracheal tubes during removal of laryngeal mask 10. Connection adapter 50 of tube retainer 48 is secured to solid rod 52 and pass through respiratory tube 26. Connection adapter 50 partially enters the proximal opening of the inserted endotracheal tube 70 as shown in FIG. 13. The length of solid rod 52 is sufficient to extend beyond the oral cavity after insertion within endotracheal tube 70, allowing manipulation of the tube retainer as needed to insure secure insertion. As shown in FIG. 13, laryngeal mask 10 may then be removed from the oropharynx without dislodging endotracheal tube 70 by sliding laryngeal mask 10 along tube retainer 48. Tube retainer 48 allows force to be exerted through solid rod 52 and connection adapter 50 on endotracheal tube 70, resisting the tendency of endotracheal tube 70 to withdraw from the laryngeal opening as laryngeal mask 10 is removed. Once clear of the oral cavity, tube retainer 48 is then removed by unscrewing it from the endotracheal tube and allowing the endotracheal tube to remain in place within the patient's laryngeal opening. Laryngeal mask 10 is simply slid off retainer 48 either before or after tube retainer 48 is removed from the endotracheal tube.

Methods of manufacturing laryngeal masks are known in the art. Any known method, including injection molding, may be used to manufacture the laryngeal masks 10 of the invention. Examples of suitable manufacturing methods are found in U.S. Pat. No. 6,261,401 to Pagan, U.S. Pat. No. 6,021,779 to Pagan and U.S. Pat. No. 5,391,248 to Brain.

What is claimed:

1. A laryngeal mask of the type used to facilitate lung ventilation and the insertion of endo-tracheal tubes or related medical instruments through a patient's laryngeal opening as used during general anesthesia, intensive care, or critical patient care, comprising:
    an inflatable positioning shield formed to fit within a patient's oropharynx, said inflatable positioning shield having an inflatable, hollow peripheral portion, a pliable posterior base in fluid communication with the peripheral portion, a shield recess formed after inflation of the peripheral portion, a rear portion formed between the posterior base and the peripheral portion after inflation of the peripheral portion, wherein the inflatable positioning shield has a recessed front portion; and
    a respiratory tube having a proximal end lumen, a curved tubular body of sufficient size to permit passage of endotracheal tubes or related medical instruments, and a distal end passing through the rear portion of the inflatable positioning shield and secured to the rear portion of the inflatable positioning shield, the distal end terminating at a distal lumen, the distal lumen passing through the peripheral portion of the inflatable positioning shield and secured to the rear portion of the inflatable positioning shield such that tubes and instruments passing through the respiratory tube will be directed into the laryngeal opening.

2. The laryngeal mask of claim 1 wherein the respiratory tube and the inflatable positioning shield are pre-curved along about the same arcuate curve such that minimal bending of the respiratory tube is required during positioning of the laryngeal mask around the laryngeal opening.

3. The laryngeal mask of claim 1 wherein the respiratory tube has an elliptical cross-section, wherein the cross-section is perpendicular to the longitudinal axis of the respiratory tube.

4. The laryngeal mask of claim 3 wherein the respiratory tube comprises a material with a low coefficient of friction to facilitate the delivery of endo-tracheal tubes or related medical instruments through the respiratory tube to the laryngeal opening.

5. The laryngeal mask of claim 4 wherein the respiratory tube comprises a material that allows it to deform radially to allow passage of endo-tracheal tubes and related medical instruments having large diameters, and return to its original elliptical cross-section shape upon the removal of said endotracheal tubes or related instruments.

6. The laryngeal mask of claim 1 wherein the distal end of the respiratory tube contained within the rear portion of the inflatable positioning shield comprises at least one additional lumen, the at least one additional lumen having a diameter that is smaller than the diameter of the distal lumen.

7. The laryngeal mask of claim 1 wherein the tubular body of the respiratory tube is of sufficient length to permit the proximal end lumen to be disposed adjacent, but external to, the oral cavity and the distal lumen to be disposed adjacent and external to the laryngeal opening.

8. The laryngeal mask of claim 1 wherein the proximal end lumen of the respiratory tube is adapted for attachment to medical devices.

9. The laryngeal mask of claim 1 wherein the peripheral portion of the inflatable positioning shield forms an essentially gap-free enclosure surrounding the laryngeal opening after inflation.

10. The laryngeal mask of claim 9 wherein the inflatable positioning shield is generally ovoid in shape after inflation.

11. The laryngeal mask of claim 1 wherein the inflatable positioning shield is secured in an airtight manner to the exterior surface of the distal end of the respiratory tube where it passes through the peripheral portion of the inflatable positioning shield.

12. The laryngeal mask of claim 11 wherein the recessed front portion of the inflatable positioning shield is in fluid communication with the distal end of the respiratory tube.

13. The laryngeal mask of claim 1 wherein the inflatable positioning shield is of sufficient size to enclose the laryngeal opening within the recessed front portion and to fit securely within the oropharynx anatomy.

14. The laryngeal mask of claim 1 wherein the recessed front portion comprises at least one support member adapted to stabilize the posterior base of the inflatable positioning shield.

15. The laryngeal mask of claim 14 wherein the at least one support member is at least one raised horizontal runner that is a continuous extension of the posterior base.

16. The laryngeal mask of claim 1 wherein the distal lumen has about the same cross-sectional shape as the respiratory tube, wherein the cross-sectional shape is defined by a perpendicular cross-section of the respiratory tube along the longitudinal axis of the respiratory tube.

17. The laryngeal mask of claim 1 wherein the distal lumen has a diameter that is smaller than the diameter of the proximal end lumen.

18. The laryngeal mask of claim 17 wherein the distal lumen comprises an upper portion and a lower portion, wherein the upper portion and the lower portion have different diameters, the diameters of both the upper portion and the lower portion are smaller than the diameter of the proximal end lumen.

19. The laryngeal mask of claim 18 wherein the distal lumen is sufficiently pliable such that it opens upon assertion of pressure thereon and returns to its original shape when the pressure is released.

20. The laryngeal mask of claim 1 wherein the distal lumen comprises an upper portion and a lower portion, the upper portion having a diameter that is different from the diameter of the lower portion.

21. The laryngeal mask of claim 20 wherein the upper portion has a diameter that is larger than the diameter of the lower portion.

22. The laryngeal mask of claim 1, wherein the recessed front portion comprises a material that is sufficiently pliable to cup the patient's trachea after inflation of the inflatable positioning shield.

23. The laryngeal mask of claim 1, wherein the peripheral portion is wedge-shaped.

24. A laryngeal mask of the type used to facilitate lung ventilation and the insertion of endo-tracheal tubes or related medical instruments through a patient's laryngeal opening as used during general anesthesia, intensive care, or critical patient care, comprising:

an inflatable positioning shield curved to fit within the anatomical structures of the oropharynx region when inflated, the inflatable positioning shield enclosing the laryngeal opening within a recessed front, and having an inflatable, hollow peripheral portion, the recessed front being sufficiently pliable to cup the patient's trachea after inflation of the inflatable positioning shield, and a rear portion formed between a posterior base and the peripheral portion after inflation of the peripheral portion; and a respiratory tube having a proximal end lumen, a curved tubular body having an elliptical cross-section, and being sufficiently radially deformable to permit passage of endo-tracheal tubes and related medical instruments there through, and a perforated distal end passing through the rear portion of the inflatable positioning shield and secured in an air-tight manner to the rear portion of the inflatable positioning shield, terminating at a distal lumen within the rear portion of the inflatable positioning shield said distal lumen passing through the peripheral portion of the inflatable positioning shield so as to be aligned axially within the laryngeal opening upon insertion into the oropharynx, wherein the cross-section is perpendicular to the longitudinal axis of the respiratory tube.

25. A laryngeal mask of the type used to facilitate lung ventilation and the insertion of endo-tracheal tubes or related medical instruments through a patient's laryngeal opening as used during general anesthesia, intensive care, or critical patient care comprising:

an inflatable positioning shield formed to fit within a patient's oropharynx, the inflatable positioning shield having an inflatable, hollow peripheral portion, a pliable posterior base in fluid communication with the peripheral portion, a shield recess formed after inflation of the peripheral portion and a rear portion formed between the posterior base and the peripheral portion after inflation of the peripheral portion, wherein the inflatable positioning shield has a recessed front portion, the recessed front portion being sufficiently pliable to cup the patient's trachea after inflation of the inflatable positioning shield, and a respiratory tube having a proximal end lumen, a curved tubular body of sufficient size to permit passage of endo-tracheal tubes and related medical instruments, therethrough, and a distal end passing through the rear portion of the inflatable positioning shield and secured to the rear portion of the inflatable positioning shield, the distal end terminating at a distal lumen, the distal lumen passing through the peripheral portion of the inflatable positioning shield and secured to the rear portion of the inflatable positioning shield such that tubes or related medical instruments passing through the respiratory tube will be directed into the laryngeal opening, wherein the distal lumen comprises an upper portion and a lower portion, the upper portion having a diameter that is different from the diameter of the lower portion.

26. A laryngeal mask of the type used to facilitate lung ventilation and the insertion of endo-tracheal tubes or related medical instruments through a patient's laryngeal opening as used during general anesthesia, intensive care, or critical patient care is provided that comprises:

an inflatable positioning shield formed to fit within a patient's oropharynx, the inflatable positioning shield having an inflatable, hollow peripheral portion, a pliable posterior base in fluid communication with the peripheral portion, a shield recess formed after inflation of the peripheral portion and a rear portion formed between the posterior base and the peripheral portion after inflation of the peripheral portion, wherein the inflatable positioning shield has a recessed front portion, the recessed front portion being sufficiently pliable to cup the patient's trachea after inflation of the inflatable positioning shield; and a respiratory tube having a proximal end lumen, a curved tubular body of sufficient size to permit passage of endo-tracheal tubes and related medical instruments, therethrough, and a distal end passing through the rear portion of the inflatable positioning shield and secured to the rear portion of the inflatable positioning shield, the distal end terminating at a distal lumen, the distal lumen passing through the peripheral portion of the inflatable positioning shield and secured to the rear portion of the inflatable positioning shield such that tubes and related medical instruments passing through the respiratory tube will be directed into the laryngeal opening, wherein the distal lumen comprises an upper portion and a lower portion, wherein the upper portion has a larger diameter than the lower portion, and wherein the distal end of the respiratory tube further comprises at least one additional lumen, the at least one additional lumen having a diameter that is smaller than the diameter of the proximal end lumen.

27. A laryngeal mask of the type used to facilitate lung ventilation and the insertion of endo-tracheal tubes or related medical instruments through a patient's laryngeal opening as used during general anesthesia, intensive care, or critical patient care is provided that comprises:

an inflatable positioning shield formed to fit within a patient's oropharynx, said inflatable positioning shield having an inflatable, hollow peripheral portion, a pliable posterior base in fluid communication with the peripheral portion, a shield recess formed after inflation of the peripheral portion, and a rear portion formed between the posterior base and the peripheral portion after inflation of the peripheral portion, wherein the inflatable positioning shield has a recessed front portion, the recessed front portion being sufficiently pliable to cup the patient's trachea after inflation of the inflatable positioning shield; and a respiratory tube having a proximal end lumen, a curved tubular body of sufficient size to permit passage of endo-tracheal tubes and related medical instruments, therethrough, and a distal end passing through the rear portion of the inflatable positioning shield and secured to the rear portion of the inflatable positioning shield, the distal end terminating at a distal lumen, the distal lumen passing through the peripheral portion of the inflatable positioning shield and secured to the rear portion of the inflatable positioning shield such that tubes and related medical instruments passing through the respiratory tube will be directed into the laryngeal opening, wherein the distal lumen comprises an upper portion and a lower portion, wherein the upper portion has larger diameter than the lower portion, wherein the distal end of the respiratory tube further comprises at least one additional lumen, the at least one additional lumen having a diameter that is smaller than the diameter of the proximal end lumen, and wherein the recessed front portion of the posterior base comprises at least one horizontal runner that is a continuous extension of the posterior base.

28. A laryngeal mask of the type used to facilitate lung ventilation and the insertion of endo-tracheal tubes or related medical instruments through a patient's laryngeal opening as used during general anesthesia, intensive care, or critical patient care, comprising:

an inflatable positioning shield formed to fit within a patient's oropharynx, said inflatable positioning shield having an inflatable, hollow peripheral portion, a pliable posterior base in fluid communication with the peripheral portion, a shield recess formed after inflation of the peripheral portion, a rear portion formed between the posterior base and the peripheral portion after inflation of the peripheral portion; and a respiratory tube having a proximal end lumen, a curved tubular body of sufficient size to permit passage of endo-tracheal tubes or related medical instruments, and a distal end passing through the rear portion of the inflatable positioning shield and secured to the rear portion of the inflatable positioning shield, the distal end terminating at a distal lumen, the distal lumen passing through the peripheral portion of the inflatable positioning shield and secured to the rear portion of the inflatable positioning shield such that tubes and instruments passing through the respiratory tube will be directed into the laryngeal opening.

29. A laryngeal mask of the type used to facilitate lung ventilation comprising a means for elevating an epiglottis without obstruction of a lumen formed by a distal end of a respiratory tube associated with the laryngeal mask.

30. A laryngeal mask having a positioning shield, the mask of the type used to facilitate lung ventilation comprising a respiratory tube having a proximal and distal end wherein the positioning shield defines a cavity with an interior surface adapted to be placed immediately adjacent to a laryngeal opening of a patient, the distal end of the respiratory tube having a majority portion projecting from the interior surface of the positioning shield into the cavity around the distal end of the respiratory tube and a minority portion formed coterminous with the interior surface of the positioning shield and terminating at a distal lumen to define the distal lumen, the distal end passing through a rear portion of the positioning shield and secured to a rear portion of the positioning shield, and the distal lumen passing through the peripheral portion of the positioning shield.

31. The laryngeal mask of claim 30 wherein the respiratory tube has an oval cross-sectional shape.

32. The laryngeal mask of claim 30 wherein the respiratory tube has a circular cross-sectional shape.

33. The laryngeal mask of claim 30 wherein the respiratory tube comprises a flexible silicone-rubber polymer.

34. The laryngeal mask of claim 30 wherein the respiratory tube comprises at least one additional lumen perforating the distal end of the tube to provide at least one alternative airway in the event that the distal lumen is obstructed.

35. A laryngeal mask of the type used to facilitate lung ventilation comprising:

an inflatable positioning shield formed to fit within a patient's oropharynx, said inflatable positioning shield having an inflatable, hollow peripheral portion, a pliable posterior base in fluid communication with the peripheral portion, a shield recess formed after inflation of the peripheral portion, a rear portion formed between the posterior base and the peripheral portion after inflation of the peripheral portion; and a respiratory tube having a proximal end lumen, a curved tubular body of sufficient size to permit passage of endo-tracheal tubes or related medical instruments, and a distal end passing through the rear portion of the inflatable positioning shield and secured to the rear portion of the inflatable positioning shield, the distal end terminating at a distal lumen, the distal lumen passing through the peripheral portion of the inflatable positioning shield and secured to the rear portion of the inflatable positioning shield such that tubes and instruments passing through the respiratory tube will be directed into the laryngeal opening, wherein the distal lumen has an upper portion and a lower portion, the upper portion having a larger diameter than the lower portion, wherein the respiratory tube comprises at least one additional lumen that perforates the distal end of the respiratory tube, the at least one additional lumen having a diameter that is smaller than the diameters of the distal lumen, and wherein the front portion of the inflatable positioning shield comprises at least one raised horizontal runner that is a continuous extension of posterior base.

36. A laryngeal mask of the type used to facilitate lung ventilation and the insertion of endo-tracheal tubes or related medical instruments through a patient's laryngeal opening as used during general anesthesia, intensive care, or critical patient care, comprising:

an inflatable positioning shield formed to fit within a patient's oropharynx, said inflatable positioning shield having an inflatable, hollow peripheral portion, a posterior base in fluid communication with the peripheral portion, a shield recess formed after inflation of the peripheral portion, a rear portion formed between the posterior base and the peripheral portion after inflation of the peripheral portion, wherein the inflatable positioning shield has a recessed front portion; and a respiratory tube having a proximal end lumen, a curved tubular body of sufficient size to permit passage of endo-tracheal tubes or related medical instruments, and a distal end passing through the rear portion of the inflatable positioning shield and secured to the rear portion of the inflatable positioning shield, the distal end terminating at a distal lumen, the distal lumen passing through the peripheral portion of the inflatable positioning shield and secured to the rear portion of the inflatable positioning shield such that tubes and instruments passing through the respiratory tube will be directed into the laryngeal opening;

wherein the distal lumen comprises a first and a second portion, said first portion having a diameter that is different from the diameter of the second portion.

37. The device of claim 36 wherein the upper portion of the distal lumen has a larger diameter than the lower portion of the distal lumen.

* * * * *